United States Patent [19]

Hallgren

[11] 4,260,802

[45] Apr. 7, 1981

[54] CATALYTIC AROMATIC SALICYLATE PROCESS

[75] Inventor: John E. Hallgren, Scotia, N.Y.

[73] Assignee: General Electric Company, Schenectady, N.Y.

[21] Appl. No.: 37,636

[22] Filed: May 11, 1979

[51] Int. Cl.$^3$ .................. C07C 69/88; C07C 68/00
[52] U.S. Cl. ................................. 560/71; 260/463; 562/406; 562/466; 562/467; 562/469
[58] Field of Search .............. 260/463; 560/71, 109

[56] References Cited

U.S. PATENT DOCUMENTS

| | | | |
|---|---|---|---|
| 3,114,762 | 12/1963 | Mador et al. | 260/463 |
| 3,227,741 | 1/1966 | Fenton | 260/463 |
| 3,444,133 | 5/1969 | Behr et al. | 260/47 ET |
| 3,625,995 | 12/1971 | Brattesani | 260/463 |
| 3,846,468 | 11/1974 | Perrotti et al. | 260/463 |
| 4,096,168 | 6/1978 | Hallgren | 260/463 |
| 4,096,169 | 6/1978 | Chalk | 260/463 |

OTHER PUBLICATIONS

Grant, Hackh's Chem. Dictionary, Fourth Edition, McGraw-Hill, NY, 1972, pp. 509, 594.

*Primary Examiner*—Glennon H. Hollrah
*Assistant Examiner*—M. C. Eakin
*Attorney, Agent, or Firm*—F. Wesley Turner; James C. Davis, Jr.; Joseph T. Cohen

[57] ABSTRACT

A catalytic aromatic salicylate process comprising contacting a phenol, carbon monoxide, a base, and a Group VIIIB element selected from ruthenium, rhodium, palladium, osmium, iridium or platinum, an oxidant having an oxidation potential greater than that of said selected Group VIIIB element, and recovering at least a portion of the resulting salicylate.

21 Claims, No Drawings

CATALYTIC AROMATIC SALICYLATE PROCESS

CROSS-REFERENCE TO RELATED APPLICATIONS

This invention is related to Alan J. Chalk's U.S. Pat. No. 4,096,169, issued June 20, 1978, and his copending U.S. Ser. No. 892,497, filed Apr. 3, 1978, now U.S. Pat. No. 4,187,242 (a continuation-in-part of U.S. patent application Ser. No. 731,495, filed Oct. 12, 1976, now abandoned) and my U.S. Pat. No. 4,096,168, issued June 20, 1978 and my copending U.S. Ser. No. 892,509, filed Apr. 3, 1978, now U.S. Pat. No. 4,201,721 (a continuation-in-part of Ser. No. 731,494, filed Oct. 12, 1976, now abandoned) and U.S. Ser. No. 834,534, filed Sept. 19, 1977, now U.S. Pat. No. 4,221,920 (a continuation of Ser. No. 731,443, filed Oct. 12, 1976, now abandoned). All of the aforesaid applications are assigned to the same assignee as the assignee of this application. All of the disclosures of the aforesaid patents and applications are incorporated herein in their entirety by reference.

BACKGROUND OF THE INVENTION

1. Field of the Invention

This invention relates to a catalytic aromatic salicylate process comprising contacting a phenol, carbon monoxide, a base, and a Group VIIIB element selected from ruthenium, rhodium, palladium, osmium, iridium or platinum, an oxidant having an oxidation potential greater than that of said selected Group VIIIB element, and recovering at least a portion of the resulting salicylate.

2. Description of the Prior Art

DESCRIPTION OF THE INVENTION

This invention embodies a catalytic aromatic salicylate process comprising contacting a phenol, carbon monoxide, a base, and a Group VIIIB element selected from ruthenium, rhodium, palladium, osmium, iridium or platinum, an oxidant having an oxidation potential greater than that of said selected Group VIIIB element, and recovering at least a portion of the resulting salicylate.

Any of the reaction parameters described in Chalk's U.S. Pat. No. 4,096,169 and copending U.S. Ser. No. 892,497, filed Apr. 3, 1978 as well as U.S. Ser. No. 731,495, filed Oct. 12, 1976 now abandoned, or my U.S. Pat. No. 4,096,168 and copending U.S. Ser. No. 892,509, filed Apr. 3, 1978 as well as U.S. Ser. No. 731,443, filed Oct. 12, 1976—now abandoned, relative to phenols (subject to the proviso set out hereafter), solvents, bases, ligands, the Group VIIIB elements, oxidants—including redox co-catalysts, etc., or reaction parameters relative to time, temperature, pressure, etc., can be employed in this invention.

Reaction parameters, preferably employed in the practice of this invention, comprise the use of (1) elevated temperatures, (2) alkali metal bases, (3) phase transfer agents, and (4) manganese redox co-catalysts.

A phenol is described herein and in the appended claims as any nuclearly hydroxy substituted aromatic compound subject to the proviso that the phenol have at least one ortho-positioned hydrogen atom relative to an —OH radical (the term "radical" may also be referred to as a "group") attached directly to an aromatic ring carbon atom. Illustratively a phenol or phenolic reactant can be described by the formula

$$R_a(OH)_x,$$

wherein $R_a$ represents an aromatic radical, —OH is a hydroxy radical attached directly to an aromatic ring carbon atom, and x is a number at least equal to 1, advantageously from 1 to 4 and preferably from 1 to 2. The $R_a$ radical can be carbo- or hetero-monocyclic, polycyclic, or fused polycyclic, and can have two or more cyclic systems (monocyclic, polycyclic, or fused polycyclic systems) which are connected to each other by single or double valence bonds, or bi- or multivalent radicals.

Preferred phenolic reactants (subject to the proviso set out herebefore) are analogous to the preferred phenolic reactants described in the aforementioned and cross-referenced Chalk and Hallgren patents and patent applications. Accordingly their descriptions are incorporated herein in their entirety by reference.

Any Group VIIIB element, defined herein in the appended claims as "the Group VIIIB element" can be employed subject to the proviso that the element be selected from ruthenium, rhodium, palladium, osmium, iridium, or platinum. The Group VIIIB element can be employed in any oxidation state, i.e. any as described in Chalk and my patent and patent applications including oxidation states including zero, i.e. their zero valent elemental metallic form, plus one, e.g., a first oxidation state greater than zero, plus two, etc.

The Group VIIIB elements can be present in ionic, inorganic or organic compound or complex, etc. forms. The Group VIIIB elements can be employed in oxide, halide, nitrate, sulfate, oxalate, acetate, carbonate, propionate, hydroxide, tartrate, etc. forms.

Group VIIIB elements in complex form, e.g., with ligands, such as carbon monoxide, nitriles, tertiary amines, phosphines, arsines, or stibines, etc., illustratively are often represented by those skilled in the art as mono-, di-, or polynuclear Group VIIIB element forms. Generally, the dimeric or polymeric forms are considered to contain Group VIIIB atoms bridged by ligands, halogens, etc. Preferred Group VIIIB elements form homogeneous mixtures when combined with the reactants, especially when the process is carried out under liquid phase reaction conditions.

The Group VIIIB elements, compounds and/or complexes can be prepared by any method known to those skilled in the art including the methods described in *Reactions of Transition-Metal Complexes*, J. P. Candlin, K. A. Taylor and D. T. Thompson, Elsevier Publishing Co. (1968) Library of Congress Catalog Card No. 67-19855, as well as those described in U.S. and foreign technical journals and patents.

As broadly stated before, any of the process parameters—including any of the various reactants as well as amount(s) of reactants—described in Chalk and my patents and patent applications can be employed in this invention. For brevity, accordingly, all of Chalk and my reaction parameters-referenced herein are incorporated herein in their entirety by reference.

Preferred reaction parameters associated with catalytic processes are described in my patent and related patent applications, e.g. the presence of substantially anhydrous reaction conditions, molecular sieves, redox co-catalysts, organic phase transfer agents, etc. For brevity, all of Chalk and my catalytic reaction parameters are incorporated herein in their entirety by reference.

(A) Illustratively, preferred reaction parameters include:
Elemental alkali or alkaline earth metal bases, e.g. lithium, sodium, potassium, calcium, or barium hydroxide; sodium, lithium or barium carbonate; sodium acetate; sodium benzoate; sodium methylate; etc.
(B) Phase transfer agents, e.g. tetrabutyl ammonium bromide, tetraethyl phosphonium iodide, tripropyl sulfonium chloride, 18-crown-6, lithium (tetramethyl ethylenediamine)$_2$ bromide, etc.
(C) Manganese redox co-catalysts of $\alpha$-diketones or $\beta$-diketones, e.g. manganese(II)bis(acetylacetonate).

Advantageously salicylate formation is enhanced as the process temperature increases since the reaction kinetics apparently increasingly favor the formation of salicylate as opposed to carbonates at elevated temperatures. Accordingly, under catalytic process conditions, optimization of salicylate is essentially temperature dependent at above about 100°–150° C., whereas under non-catalytic process conditions—as described in my copending application—optimization of salicylate is significantly effected by the Group VIIIB element oxidation state.

Aromatic salicylates can be generically described by the following formula:

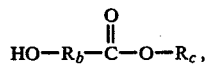

wherein $R_b$ represents an aromatic radical with the hydroxyl radical positioned ortho relative to the carboxylate, i.e.

radical associated with an aromatic $R_c$ radical. The $R_b$ and $R_c$ radicals can be carbo- or hetero-monocyclic, polycyclic, or fused polycyclic, and can have two or more cyclic systems (monocyclic, polycyclic or fused polycyclic systems) which are directly joined to each other by single or double valence bonds, or by bi- or multivalent radicals.

In order that those skilled in the art may better understand my invention, the following examples are given which are illustrative of the best mode of this invention, however, these examples are not intended to limit the invention in any manner whatsoever. Unless otherwise specified, all parts are by weight and the reaction products were verified by infrared spectrum, C-13 nuclear magnetic resonance and mass spectrometry.

EXAMPLE I

Preparation of phenyl salicylate using palladium(II)-dichloride as the Group VIIIB compound and copper-(II)dichloride as the oxidant under carbon monoxide pressure.

A reaction vessel was charged with 94 g. (1.0 mole) of phenol, 34.0 g. (0.25 mol) of copper(II)dichloride, 0.45 g. (0.0025 mol) of palladium(II)dichloride, 147 g. (0.75 mol) of dicyclohexyl-N-methylamine, and 500 ml. of methylene chloride. The mixture was pressurized with 420 psig CO and heated to 160° C. for 4 hours, cooled and vented. Gas chromatography established the presence of 10.7 g. of phenyl salicylate (5% conversion based on phenol, 40% yield based on CuCl$_2$).

EXAMPLES II–III

Preparation of 4-($\alpha,\alpha$-dimethylbenzyl)phenyl 5-($\alpha,\alpha$-dimethylbenzyl)-2-hydroxy benzoate using p-cumylphenol, carbon monoxide, aqueous sodium hydroxide, palladium(I)bromide, manganese(II)bis(acetylacetonate), a Type 3A molecular sieve, a phase transfer agent, at 25° C. and 180° C.

A 21 ml. Hastelloy-C autoclave was charged with a spin (stir) bar, 2.12 g. (10.0 mmol.) of p-cumylphenol, 0.045 g. (0.75 mmol.) of a 50% aqueous sodium hydroxide solution, 0.013 g. (0.05 mmol.) of palladium(I)bromide, 0.038 g. (0.15 mmol.) of manganese(II)bis(acetyl acetonate), 3.0 g. of Linde 3A molecular sieves which had been activated by heating to 200° C. in a stream of dry nitrogen for 24 hours, 0.327 g. (1.0 mmol.) of tetrabutyl ammonium bromide, 0.125 g. of bibenzyl, and 12 ml. of methylene chloride. The resulting mixture was pressurized to 1,000 psig (550 psig via carbon monoxide and 450 psig via air), heated to 180° C. for 20 minutes, and cooled to room temperature overnight. Attempts to prepare 4-($\alpha,\alpha$-dimethylbenzyl)phenyl 5-($\alpha,\alpha$-dimethylbenzyl)-2-hydroxybenzoate under reaction conditions similar to those described in this Example—with the exception of illuminating the 180° C. heating step—were unsuccessful. Liquid chromatography established the presence and the amount(s) of the reaction products noted in Table I hereafter:

TABLE I

| Run No. | Reaction Temperature(s) | Reaction Time | Salicylate Species* | /Amount/Yield % | Carbonate Species* | /Amount/Yield |
|---|---|---|---|---|---|---|
| 1 | 25° C. | 19 hrs. | A | /none/none | B | /0.733g./34% |
| 2 | 180° C. | 19 hrs. | A | /0.448g./19.9% | B | /0.304g./13.5% |

*-Species A = 4-($\alpha,\alpha$-dimethylbenzyl)phenyl-5-($\alpha,\alpha$-dimethylbenzyl)-2-hydroxybenzoate of the formula

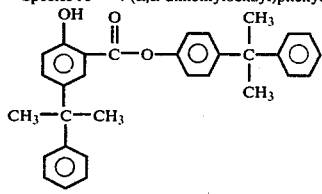

*-Species B = 4,4'-($\alpha,\alpha$-dimethylbenzyl)diphenyl carbonate of the formula

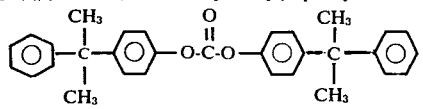

In the practice of my process, the Group VIIIB elements after separation from the resulting reaction products can be oxidized or reduced to any suitable oxidation state, and can be re-employed, that is, recycled in the aromatic salicylate process described herein.

Although the above examples have illustrated various modifications and changes that can be made in carrying out my process, it will be apparent to those skilled in the art that other changes and modifications can be made in the particular embodiments of the invention described which are within the full intended scop of the invention as defined by the appended claims.

I claim:

1. A catalytic process for the preparation of (1) an aromatic salicylate of the formula

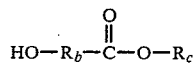

wherein the $R_b$ and $R_c$ radicals are derived from the aromatic $R_a$ portion of the phenol of the formula $R_a$—$(OH)_x$ defined hereafter wherein $R_b$ represents an aromatic radical with a hydroxyl radical positioned ortho relative to the carboxylate radical associated with the aromatic $R_c$ radical, wherein independently each $R_b$ and $R_c$ is a carbo-monocyclic, carbo-polycyclic or fused carbo-polycyclic radical which comprises (2) contacting a phenol of the formula $R_a$—$(OH)_x$, wherein $R_a$ is a carbo-monocyclic, carbo-polycyclic, or fused carbo-polycyclic aromatic radical, x is a number at least equal to 1, carbon monoxide, a base, and a Group VIIIB element selected from ruthenium, rhodium, palladium, osmium, iridium or platinum, and an oxidant having an oxidation potential greater than that of the Group VIIIB element wherein the reaction is carried out at a temperature of at least about 100° C.

2. The claim 1 process, further comprising a solvent.

3. The claim 1 process, wherein said element is present in an ionic form.

4. The claim 1 process, wherein said element oxidation state is at least +1.

5. The claim 1 process, wherein said base is a sterically hindered amine.

6. The claim 1 process, wherein said element is associated with a carbonyl group.

7. The claim 1 process, wherein said element is associated with a halide.

8. The claim 1 process, wherein said element is coordinated with a ligand selected from an arsine, a stibene, a phosphine, a nitrile or a halide.

9. The claim 1 process, wherein said element is associated with an inorganic halide compound.

10. The claim 1 process, wherein said element oxidation state is zero.

11. The claim 1 process, wherein said element oxidation state is +2.

12. The claim 1 process, further comprising a redox co-catalyst.

13. The claim 1 process, further comprising substantially anhydrous reaction conditions.

14. The claim 1 process, further comprising a phase transfer agent.

15. The claim 13 process, further comprising a drying agent.

16. The claim 15 process, wherein the drying agent is a molecular sieve.

17. The claim 14 process, wherein the phase transfer agent is an onium halide.

18. The claim 14 process, wherein the base is an alkali metal hydroxide.

19. The claim 1 process, wherein the element is palladium.

20. The claim 19 process, wherein the Group VIIIB element is a form of palladium having an oxidation state of +1.

21. The claim 19 process, wherein the Group VIIIB element is a form of palladium having an oxidation state of +2.

* * * * *